United States Patent
Volden

(10) Patent No.: US 8,137,709 B1
(45) Date of Patent: Mar. 20, 2012

(54) FAST-HELP NAUSEA RELIEF

(76) Inventor: Gerald Volden, Lakeland, FL (US)

( * ) Notice: Subject to any disclaimer, the term of this patent is extended or adjusted under 35 U.S.C. 154(b) by 228 days.

(21) Appl. No.: 12/635,158

(22) Filed: Dec. 10, 2009

(51) Int. Cl.
*A01N 65/00* (2009.01)

(52) U.S. Cl. ....................................................... 424/725

(58) Field of Classification Search ......................... None
See application file for complete search history.

(56) References Cited

U.S. PATENT DOCUMENTS

| | | |
|---|---|---|
| D271,536 S | 11/1983 | Siecke |
| 6,793,942 B2 | 9/2004 | Gelber et al. |
| 7,163,705 B2 | 1/2007 | Johnson et al. |
| 7,250,181 B2 | 7/2007 | Ghosal |
| 2006/0051455 A1 | 3/2006 | Andersen et al. |
| 2007/0048367 A1 | 3/2007 | Kaderali |

*Primary Examiner* — Michael Meller

(57) ABSTRACT

The fast-help nausea relief medicinal composition provides a fast-acting formula that is composed of all natural ingredients, which treat nausea associated with hangovers and motion sickness. The fast-help nausea relief is comprised of ginger root, gelatin, a fruit flavoring, and mint. The fast-help nausea relief composition, once cooked, can be applied to varying consuming mediums comprising a chewing gum, a pop-sickle, a freezer pop, a gummy chew, a gelatin cup, a gel strip, or as a drink.

1 Claim, 2 Drawing Sheets

FAST-HELP NAUSEA RELIEF

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

A. Field of the Invention

The present invention relates to the field of nausea relieving formulas, more specifically, a fast-acting, all-natural formula that relieves nausea and vomiting due to motion sickness or hangovers.

B. Discussion of the Prior Art

As a preliminary note, it should be stated that there is an ample amount of prior art that deals with nausea relieving formulas. As will be discussed immediately below, no prior art discloses a fast-acting formula that is made of all-natural ingredients, of which involves the cooking instructions discussed below, and is effective in treating nausea due to motion sickness or hangovers.

The Ghosal Patent (U.S. Pat. No. 7,250,181) discloses pharmaceutical compositions of poly-herbal extracts useful as root and plant extracts as well as gelling agents. However, the ingredients do not include a fruit flavoring as well as mint, and wherein the ingredients are prepared and can be instilled in a plurality of consuming mediums.

The Kaderali Patent Application Publication (U.S. Pub. No. 2007/0048367) discloses an herbal composition for treating morning sickness that includes the ingredients of ginger root extract and fructose. However, the herbal composition does not include mint or a fruit flavoring.

The Gelber et al. Patent (U.S. Pat. No. 6,793,942) discloses an anti-nausea medicinal composition with ginger root. However, the medicinal composition does not include mint, fruit flavoring, or a gelatin base.

The Andersen Patent Application Publication (U.S. Pub. No. 2006/0051455) discloses a chewing gum tablet having medicinal properties and of which includes fructose, ginger, and gelatin. However, the chewing gum tablet does not include mint, or comprise the steps as outline below for production thereof.

The Johnson et al. Patent (U.S. Pat. No. 7,163,705) discloses a chewing gum that can be used to treat coughs, colds, and motion sickness. However, the chewing gum does not include the ingredients of ginger, gelatin, mint, and fruit flavoring to provide an anti-nausea compound that is both fast-acting and all-natural.

While the above-described devices fulfill their respective and particular objects and requirements, they do not describe a fast-acting formula that is made of all-natural ingredients, of which involves the cooking instructions discussed below, and is effective in treating nausea due to motion sickness or hangovers. In this regard, the fast-help nausea relief departs from the conventional concepts and designs of the prior art.

SUMMARY OF THE INVENTION

The fast-help nausea relief medicinal composition provides a fast-acting formula that is composed of all natural ingredients, which treat nausea associated with hangovers and motion sickness. The fast-help nausea relief is comprised of ginger root, gelatin, a fruit flavoring, and mint. The fast-help nausea relief composition, once cooked, can be applied to varying consuming mediums.

An object of the invention is to provide a nausea relief composition that is made of all natural ingredients.

A further object of the invention is to provide a nausea relief composition that is fast-acting.

A further object of the invention is to provide a nausea relief composition that can be applied to a plurality of consuming mediums comprising a chewing gum, pop-sickle, freezer pop, gummy chew, gelatin cup, gel strip, or as a drink.

These together with additional objects, features and advantages of fast-help nausea relief will be readily apparent to those of ordinary skill in the art upon reading the following detailed description of presently preferred, but nonetheless illustrative, embodiments of the fast-help nausea relief when taken in conjunction with the accompanying drawings.

In this respect, before explaining the current embodiments of the fast-help nausea relief in detail, it is to be understood that the fast-help nausea relief is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the fast-help nausea relief. It is therefore important that the claims be regarded as including such equivalent construction insofar as they do not depart from the spirit and scope of the fast-help nausea relief. It is also to be understood that the phraseology and terminology employed herein are for purposes of description and should not be regarded as limiting.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE EMBODIMENT

Figures 1, 2:
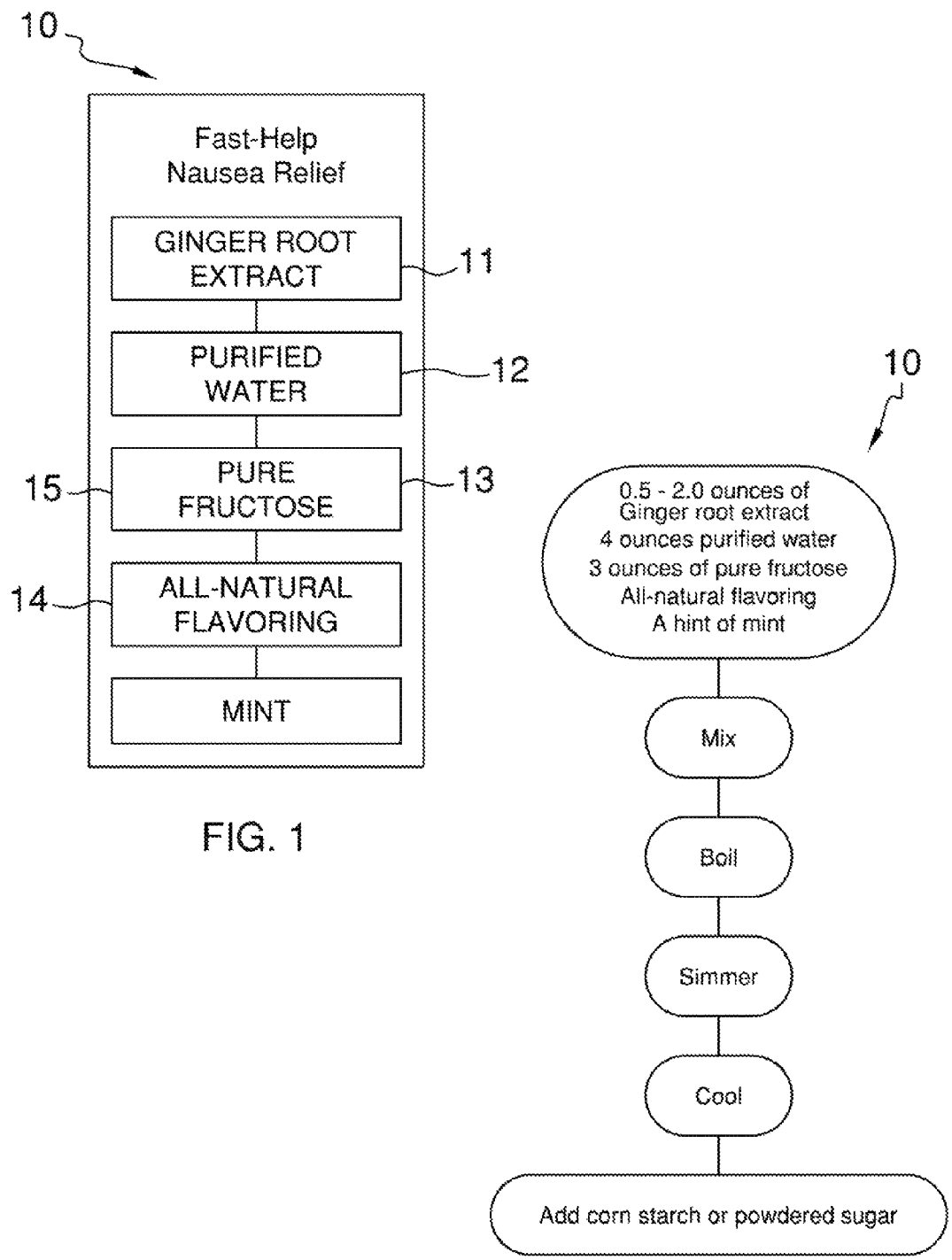
FIG. 1 illustrates a list of ingredients comprising the fast-help nausea relief.
FIG. 2 illustrates a diagram listing the instructions for preparing the fast-help nausea relief in a gelatin form wherein the ingredients are mixed together, boiled, simmered, cooled, and added with corn starch or powdered sugar.
Figure 3:
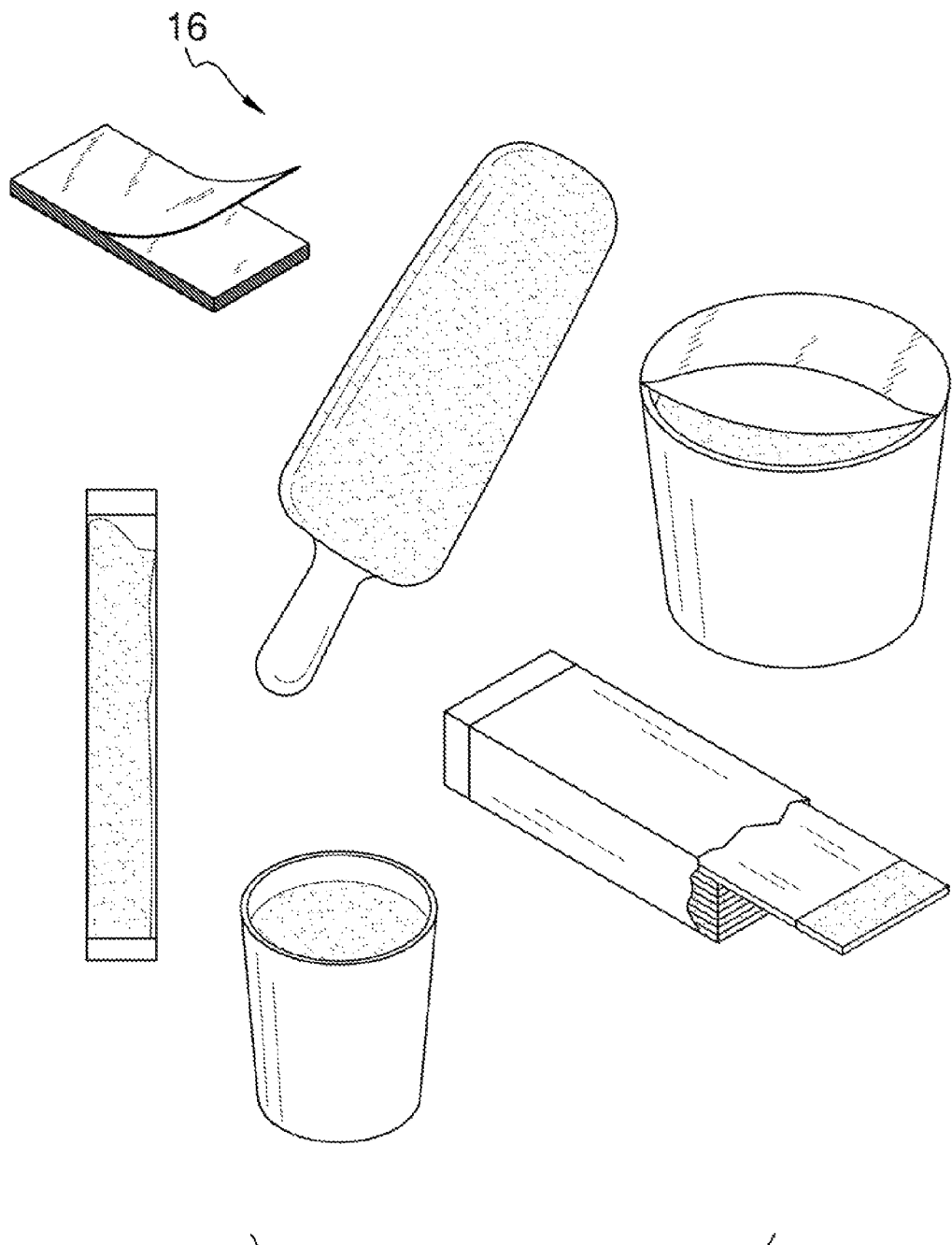
FIG. 3 illustrates the various consuming means.

Detailed reference will now be made to the preferred embodiment of the present invention, examples of which are illustrated in FIGS. 1-3. A fast-help nausea relief 10 (hereinafter invention) includes a plurality of ingredients comprising ginger root extract 11, water 12, purified fructose 13, mint 14, and flavoring means 15.

Referring to FIG. 2, the amounts of each ingredient are proscribed, along with the directions for preparing the invention 10 in a gelatin-based consuming means. It shall be noted that the base ingredients for the invention 10 are water, mint 14, ginger root extract 11, and fructose 13. The flavoring means 15 are secondary ingredients that provide flavoring. The flavoring means 15 are depicted as all-natural flavoring.

The ingredients are mixed, boiled, simmered down, cooled, and powered by a powering agent such as cornstarch or powdered sugar.

It is being asserted that the ingredients, when mixed and prepared, provide a nausea-relieving compound that is both fast acting and comprised of all natural ingredients. It is further being asserted that the combination of a ginger root, mint, and gelatin base provide natural medicinal qualities that aid in calming a stomach down when disrupted via motion sickness or from a hangover.

The flavoring means 15 may comprise a fruit flavoring, a root beer flavoring, a black cherry flavoring, a mint flavoring, an ice cream flavor flavoring, or a chewing gum flavor flavoring. It is being asserted through trials conducted by the inventor, that the use of black cherry flavoring with the mint flavor has the most soothing effect when compared to other powdered gelatin forms of flavoring means 15. It shall be noted that the inclusion of the flavoring means 15 hides or masks the burn or heat generated when the ginger root extract 11 is ingested into the stomach.

It shall be noted that the flavoring means 15 may be in powdered form of flavored gelatin (akin to JELLO powdered form). However, it shall be noted that the specified flavor of the flavoring means 15 may be in the form of 6 ounces of juice, which would alleviate the need for the purified water 12. It shall be further noted that the specified flavor of the flavoring means 15 may be in the form of a concentrated juice, which would not alleviate the need for the purified water 12, but would reduce the overall amount of the purified water 12.

A gelatin-based embodiment (gummy chew or gel strip) of the invention 10 is prepared by adding 0.5 to 2.0 ounces of ginger root extract 11, 6 ounces of purified water 12, 3 ounces of pure fructose 13 (please note that the pure fructose may be in syrup form), ¼ cup mint leaves 14, and 1 ounce of flavoring means 15. Begin by mixing the 6 ounces of purified water 12, 0.5 to 2.0 ounces of ginger root extract 11, and ¼ cup of mint leaves 14. Next, bring the mixture to a rapid boil for 1 to 2 minutes, and strain out all of the excess water. Mix in 3 ounces of pure fructose 13 and 1 ounce of powdered flavored Gelatin form of the flavoring means 15. Boil the mixture until the mixture is totally melted, and then pour onto a flat, clean surface and let cool to room temperature. Now the remaining mixture can be cut into gummy squares, or spread thin to form a gel strip. After the desired consuming medium is formed, the mixture is dusted with a corn-starch or powdered sugar to prevent sticking.

To make a gelatin cup embodiment, begin by mixing the 6 ounces of purified water 12, 0.5 to 2.0 ounces of ginger root extract 11, and ¼ cup of mint leaves 14. Next, mix in pure fructose 13 and the flavoring means 15 (consisting of 1 ounce of powdered gelatin form), and bring the mixture to a rapid boil for 1 to 2 minutes. Next, place said mixture in a refrigerated environment until the mixture gels into a gelatin consuming means. Please note the difference required to make the gelatin cup is to not strain excess water after boiling, but to then place the mixture in a refrigerator or refrigerated environment to gel.

In non-gelatin based embodiments, the invention 10 is prepared, boiled, simmered, cooled, and applied to one of the remaining consuming mediums 16, as outlined in FIG. 3, comprises a chewing gum, pop-sickle, freezer pop, or as a drink. The non-gelatin based embodiments of the invention 10 do not strain out excess water as the mixture remains in liquid form in order to be mixed with a chewing gum base, frozen to make pop-sickle or freezer pop, or as a drink. Also, the non-gelatin based embodiments may substitute the powdered gelatin form of flavoring means 15 with a juice (excluding the water 12) or a juice concentrate (concentrate having a ratio of 1 part juice concentrate to 3.5 parts water 12).

With respect to the above description, it is to be realized that the optimum dimensional relationship for the various components of the invention 10, to include variations in size, materials, shape, form, function, and the manner of operation, assembly and use, are deemed readily apparent and obvious to one skilled in the art, and all equivalent relationships to those illustrated in the drawings and described in the specification are intended to be encompassed by the invention 10.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A nausea relief medicinal composition consisting of 0.5 to 2.0 ounces of ginger root extract, 6 ounces of water, 3 ounces of fructose, 1 ounce of a powdered gelatin, mint leaves and black cherry flavoring.

* * * * *